United States Patent [19]

Schep

[11] 4,294,977
[45] Oct. 13, 1981

[54] PROCESS FOR PRODUCING AROMATIC CARBOXYLIC ACIDS

[75] Inventor: Raymond A. Schep, Newport Beach, Calif.

[73] Assignee: Occidental Research Corporation, Irvine, Calif.

[21] Appl. No.: 78,401

[22] Filed: Sep. 24, 1979

Related U.S. Application Data

[63] Continuation of Ser. No. 883,933, Mar. 6, 1978, abandoned.

[51] Int. Cl.³ .............................................. C07C 51/21
[52] U.S. Cl. ...................................... 562/407; 562/513
[58] Field of Search ............... 562/407, 412, 414, 417, 562/513

[56] References Cited

U.S. PATENT DOCUMENTS

| | | | |
|---|---|---|---|
| 2,193,337 | 3/1940 | Leicester | 260/538 |
| 2,461,740 | 2/1949 | Kiebler | 260/515 |
| 2,555,410 | 6/1951 | Howard | 260/515 |
| 2,785,198 | 3/1957 | Grosskinsky et al. | 260/525 |
| 2,786,074 | 3/1957 | Goren | 562/407 |
| | | Grossknsky et al. | |
| 2,833,816 | 5/1958 | Saffer et al. | 260/524 |
| 2,948,750 | 8/1960 | Blaser et al. | 260/515 |
| 2,981,751 | 4/1961 | Keith et al. | 562/412 |
| 3,023,216 | 2/1962 | Blaser et al. | 260/295.5 |
| 3,023,217 | 2/1962 | Stein et al. | 260/295.5 |
| 3,064,043 | 11/1962 | Taylor et al. | 260/523 |
| 3,064,046 | 11/1962 | Taylor et al. | 260/523 |
| 3,259,650 | 7/1966 | Decker et al. | 260/515 |
| 3,468,943 | 9/1969 | Creighton et al. | 260/523 |
| 3,529,020 | 9/1970 | Landis | 562/417 |
| 3,558,458 | 1/1971 | Block | 204/158 |
| 3,702,340 | 11/1972 | Selin et al. | 260/515 H |
| 3,709,931 | 1/1973 | Proell et al. | 260/515 H |

FOREIGN PATENT DOCUMENTS 35-18365 of 1960 Japan.

OTHER PUBLICATIONS

Zh. Prikl, Khim, vol. 38, No. 12, p. 2779 (1965).
Bearse, A. E. et al. "Production of Chemicals by Oxidation of Coal" A Battelle Energy Program Report, Mar. 31, 1975.
U.S. Bureau of Mines Information Circular No. 8234, pp. 74 to 98.
Franke, N. W. et al. "Water-Soluble Polycarboxylic Acids by Oxidation of Coal." Ind. Eng. Chem., vol. 44, pp. 2784-2792 (1952).
Montgomery, R. S. et al. "The Caustic-Oxygen Oxidation of Bituminous Coal." U.S. Bureau of Mines Information Circular No. 8234, pp. 74-98.
Kirk-Othmer "Encyclopedia of Chemical Technology." 1st Ed. (1950) vol. 4 at pp. 86, 87 and 94.

*Primary Examiner*—Joseph E. Evans
*Assistant Examiner*—L. Hendriksen
*Attorney, Agent, or Firm*—Forrest E. Logan

[57] ABSTRACT

A process for producing a carboxylic acid salt from carbonaceous material comprising treating a mixture of a carbonaceous material which is essentially free of minerals from oil shale, water, and a material containing minerals from oil shale with oxygen under conditions sufficient to convert said carbonaceous material to a carboxylic acid salt.

The carboxylic acid salt can be converted to a carboxylic acid.

The process is especially useful for producing an aromatic carboxylic acid from an aromatic carbonaceous material such as coal.

27 Claims, 1 Drawing Figure

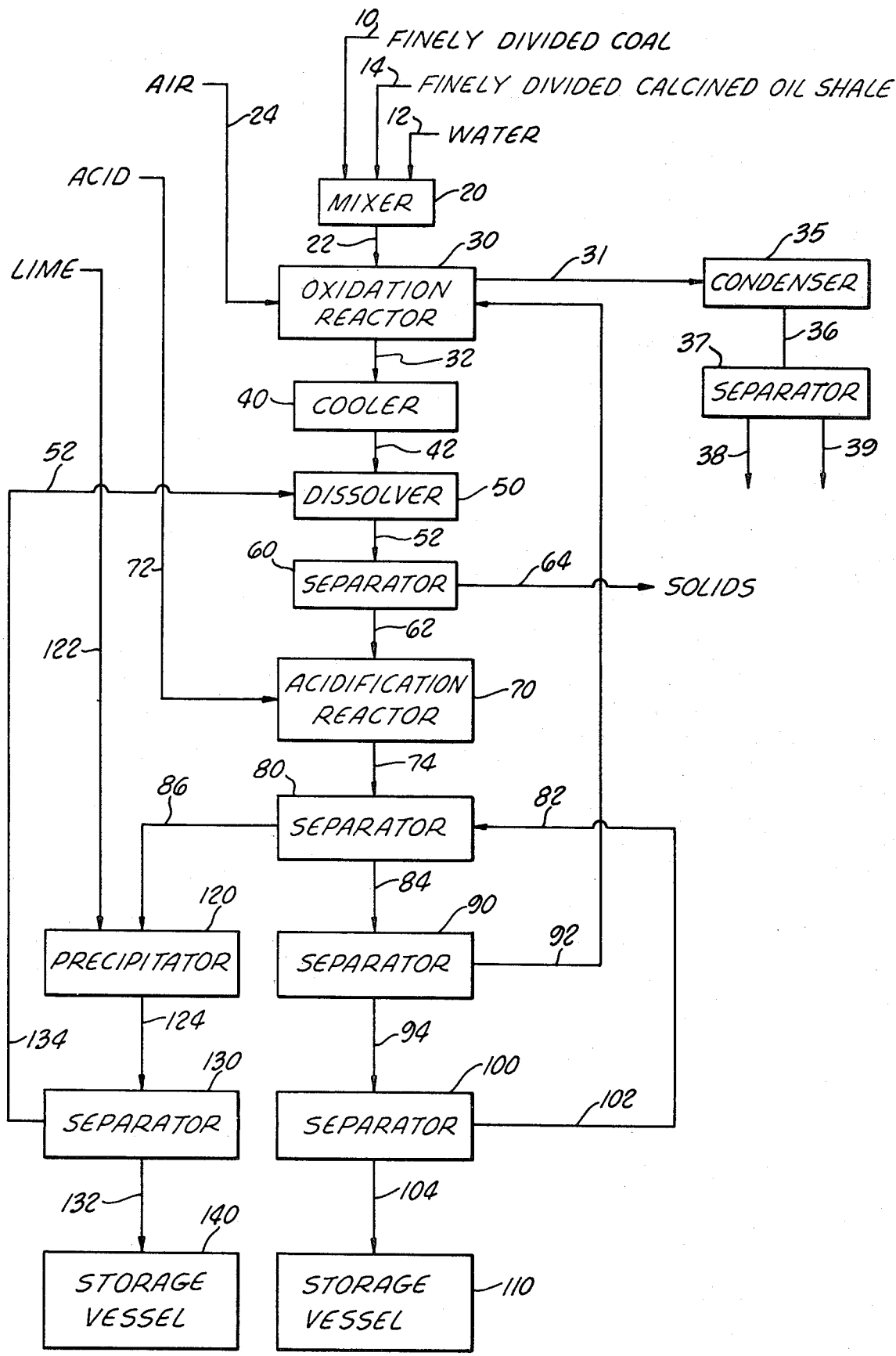

PROCESS FOR PRODUCING AROMATIC CARBOXYLIC ACIDS

This is a continuation of application Ser. No. 883,933, filed Mar. 6, 1978 now abandoned.

FIELD OF INVENTION

The field of the invention relates to the production of carboxylic acid salts and their carboxylic acids from carbonaceous materials and especially to the production of aromatic carboxylic acids from aromatic materials, such as coal, petroleum residium, shale oil, and tar sands. The invention is particularly useful for the production of benzene carboxylic acids from bituminous coal.

PRIOR ART

U.S. Pat. No. 2,785,198 discloses a process for producing polycarboxylic acids from bituminous coal, lignites, peat and the like or their carbonization products such as coal, tar, or pitch by thermal treatment with oxidizing agents such as nitric acid, chromic acid, permanganate, or oxygen or air under super-atmospheric pressure in an alkaline medium.

The crude oxidation product is subject to an extraction treatment with a polar organic solvent for both the monocyclic aromatic and high molecular weight polycarboxylic acids, and treating the thusly formed solution with water to extract the monocyclic aromatic polycarboxylic acids from the remainder of the mixture.

The alkaline medium disclosed is sodium hydroxide.

U.S. Pat. No. 2,193,337 discloses a process for producing organic acids by heating carbonaceous material such as sawdust, wood chips, peat, or coal with oxygen-containing gases at elevated pressures and temperatures in the presence of at least 10 times the weight of the carbonaceous material of water and preferably an oxide or hydroxide of an alkali or alkaline earth metal. Oxalic acid and other organic acids which are formed, such as mellitic and benzoic acid or acetic acid, may be isolated from the resulting reaction mixture as salts of the alkali or alkaline earth metals. The caustic material disclosed is an oxide or hydroxide of an alkali metal or an alkaline earth metal and specifically lime, quick-lime, and caustic soda.

U.S. Pat. No. 2,786,074 discloses a process for making organic acids by oxidizing carbonaceous materials at elevated temperatures and pressures with gaseous oxygen in the presence of an alkaline solution. Alkalis which are suitable for use in a high pressure reactor are specified as sodium hydroxide, potassium hydroxide, and mixtures thereof.

U.S. Pat. No. 2,461,740 discloses a process for oxidizing carbonaceous material to aromatic acids using a two-stage oxidation process.

In the first stage, the carbonaceous material is oxidized to a state where it is soluble in aqueous alkali such, for example, as a solution of sodium hydroxide, potassium hydroxide, sodium carbonate, or potassium carbonate, especially at elevated temperatures.

Any acid or acid anhydride with suitable oxidizing properties which can be regenerated by air and recycled in the process can be employed, for example sulfur trioxide, oxides of nitrogen, or the acids formed by reaction of these compounds with water. Specifically disclosed are sulfur trioxide, $N_2O_3$, and $N_2O_5$.

In the second stage, the use of a high pressure elevated temperature reaction of oxygen gas in aqueous alkali is disclosed. The aqueous alkali employed is a solution of sodium hydroxide, potassium hydroxide, sodium carbonate, or potassium carbonate.

U.S. Pat. No. 3,023,217 discloses a process for introducing carboxyl groups into aromatic compounds free from carboxyl groups, such as aromatic carbocyclic hydrocarbons and aromatic heterocyclic hydrocarbons. The patent discloses a process for introducing into aromatic carbocyclic or aromatic heterocyclic compounds free from carboxyl groups by reacting such materials in the absence of substantial amounts of oxygen, such as a non-oxidative atmosphere and under anhydrous conditions with alkali metal salts of aliphatic carboxylic acids at elevated temperatures and pressures in the presence of catalysts. As disclosed in the process, it is necessary to exclude the presence of substantial quantities of oxygen. Examples of aliphatic carboxylic acids which are used in the form of their alkali metal salts, especially their potassium salts, are oxalic acid, malonic acid, maleic acid, and trichloroacetic acid.

Examples of suitable compounds free from carboxyl groups which may be used as starting materials for the process are aromatic carbocyclic compounds free from carboxyl groups such as monocyclic aromatic hydrocarbons such as benzene or its derivatives having saturated alkyl or cycloalkyl substitutes attached thereto, and dicyclic aromatic hydrocarbons such as naphthalenes, diphenyl, and other polycyclic aromatic hydrocarbon compounds. Similarly, aromatic heterocyclic compounds free from carboxyl groups which may be used as starting materials are heterocyclic compounds which contain one or more heteroatoms in the ring and which are designated as having an aromatic character because of their chemical behavior.

U.S. Pat. No. 2,948,750 discloses a process for carboxylating aromatic hydrocarbons by direct introduction of carbon dioxide to produce polycarboxylic acids.

Suitable starting materials which are disclosed are aromatic hydrocarbons, especially benzene but also toluene, xylene, cumene and diisopropyl benzene and other benzenes substituted with saturated or unsaturated alkyl or cycloalkyl radicals, napthalene, diphenyl, diphenylmethane and other aromatic compounds which may also be substituted with hydrocarbon radicals.

Selective carboxylation is accomplished by heating the starting materials in the presence of an acid-binding agent, and carbon dioxide under anhydrous conditions. Examples of the acid-binding agent are carbonates of alkali metals, especially potassium carbonate, the salts of other weak acids such as bicarbonates, formates, or oxalates. Similarly, the corresponding compounds of other metals are suitable; for example, the carbonates of the alkali earth metals.

U.S. Pat. No. 3,023,216 discloses a method of introducing carboxyl groups into aromatic carbocyclic compounds free from carboxyl groups by reacting these compounds in a non-oxidative atmosphere with alkali metal salts of aromatic carbocyclic or aromatic heterocyclic carboxylic acids.

Suitable compounds which are free from carboxyl groups which may be used as starting compounds in this patent are similar to the starting compounds in U.S. Pat. No. 2,948,750.

U.S. Pat. No. 3,023,216 discloses reacting aromatic carbocyclic compounds free from carboxyl groups with aromatic carboxylic acids in the form of their alkali metal salts.

Both U.S. Pat. Nos. 3,023,216 and 2,948,750 require essentially specific chemical compounds as starting materials.

U.S. Pat. No. 2,833,816 discloses a process for oxidizing aromatic compounds using a catalyst comprising a lower aliphatic carboxylate salt of a heavy metal and bromine. Examples of a heavy metal are manganese, cobalt, nickel, chromium, vanadium, molybdenum, tungsten, tin, and cerium.

The metals may be supplied in the form of metal salts; for example such as manganese acetate. The bromine may be supplied as ionic bromine, or other bromine compounds soluble in the reaction medium such as potassium bromate.

Thus, the process requires the conjoint presence of bromine and a heavy metal oxidation catalyst.

The starting material required is an aromatic compound containing one or more aliphatic substituents to produce corresponding aromatic carboxylic acids.

U.S. Pat. No. 3,064,043 discloses a process for oxidizing para-toluic acid or para-formyl toluene to produce terephthalic acid.

U.S. Pat. No. 3,064,046 discloses a process for oxidizing toluic acid or formyl toluene to produce orthophthalic acid or isophthalic acid.

Both U.S. Pat. Nos. 3,064,043 and 3,064,046 require specific starting materials to be oxidized.

U.S. Pat. No. 3,558,458 discloses a process for preparing aromatic acids by treating an alkyl aryl ketone with water at an elevated temperature in the presence of a reaction promoting agent. The reaction promoting agent may comprise an alkaline catalyst, a transition metal salt, or actinic light. Examples of an alkaline catalyst include potassium acetate, lithium acetate, rubidium acetate, and cesium acetate. The process is conducted in water at a temperature of about 200° C. to 400° C.

The art dicloses processes for the alkaline oxidation of coal employing large amounts of chemicals relative to the amount of water soluble coal acids produced, see U.S. Pat. No. 2,786,074 and a report entitled "Production of Chemicals by Oxidation of Coal", Battelle Laboratory, Columbus, Ohio of Mar. 31, 1975. This report also suggests the use of potassium acetate and acetic acid in a cyclic process for the Henkel reaction of page 19. The substance of the Battelle Report is incorporated herein by reference.

Recovery of caustic soda and sodium carbonate was disclosed by Industrial and Engineering Chemistry, Volume 44 (1952), at page 2791 in an article entitled "Water-Soluble Polycarboxylic Acids by Oxidation of Coal" beginning at page 2784.

Japanese Patent Disclosure 18,365 discloses the reclamation of alkali by recrystallization and requires the consumption of one part by weight of the alkali and 1.5 parts of sulfuric acid for each two parts of coal consumed.

Non-alkaline oxidation of coal generally yields about 10 parts by weight of water soluble coal acids based on 100 parts of coal carbon consumed. Alkaline oxidation yields have been about 30 to about 42 parts per 100 parts of coal carbon consumed. Therefore, alkaline oxidation processes are favored because of the higher yield possible.

In systems like $HCl/KCl$, $H_2SO_4/K_2SO_4$, and $HNO_3/KNO_3$ the salts do not produce an alkali solution by hydrolysis because the acids involved are too strong.

These systems over oxidize the coal and therefore result in much lower yield of coal acids.

Another disadvantage of treatment of coals with strong acids is the production of unwanted by-products by chlorination, sulfation, or nitration of the aromatic nuclei of the coal.

Coal acids have been prepared by nitric acid oxidation, U.S. Pat. Nos. 3,468,943; 3,709,931; 2,555,410; in the presence of nitrogen catalyst, U.S. Pat. No. 3,702,340; and oxidation in a non-alkaline aqueous medium, U.S. Pat. No. 3,259,650.

The caustic-oxygen treatment of coal has been described in U.S. Bureau of Mines Information Circular No. 8234 at pages 74 to 98.

In another process, U.S. Pat. No. 3,259,650 discloses the use of a non-alkaline medium and produces lower yields of water soluble coal acids.

Although oxidation can be carried out in reclaimable acidic media, these processes are not as desirable because of lower yields and unwanted by-products due to chlorination, sulfation, and nitration.

When oil shales are oxidized by atmospheric oxygen in an alkaline medium dicarboxylic acids are formed, in addition to monocarboxylic and high-molecular acids, as reported in Zh. Prikl. Khim., Vol. 38, No. 12, p. 2779 (1965).

The applicant's invention allows for an economical and high yield of carboxylic acids from carbonaceous material. In particular, in the applicant's invention, can produce aromatic carboxylic acids from aromatic material such as bituminous coal.

SUMMARY OF THE INVENTION

This invention provides an improved process for the production of carboxylic acids from carbonaceous materials.

A mixture of carbonaceous material which is essentially free of minerals from oil shale, water, and a material containing minerals from oil shale, such as a calcined oil shale, is first formed. Preferably, the material containing minerals from oil shale is finely divided. Preferably, the mixture is such that it will produce an alkaline solution by hydrolysis. Mixtures which produce an alkaline solution by hydrolysis result in a higher yield of carboxylic acids.

The carbonaceous material may be coal, lignite, peat, coke, char, and other materials containing, or capable of evolving, or producing, a hydrocarbon material, either liquid or solid.

Pure water is not required and in fact process water may be used over at least in part.

The mixture can be formed in any manner in a mixing zone using mixers suitable for handling slurries containing solids.

The mixture is removed from the mixing zone and fed to an oxidation-reaction zone wherein the mixture is reacted with oxygen, or an oxygen-containing gas such as air. The oxidation-reaction zone and the mixing zone can be, if desired, in the same vessel, as may be advantageous in a batch-type process, or they may be in separate vessels as required for a continuous process.

More particularly, this invention provides an improved process for the production of aromatic carboxylic acids from aromatic materials. In this case, a mixture of an aromatic material essentially free of minerals from oil shale, water, and a material containing minerals from oil shale, such as calcined oil shale, is first formed. As described above, preferably the mixture is such that it will produce an alkaline solution by hydrolysis. Mixtures which produce an alkaline solution by hydrolysis result in a higher yield of aromatic carboxylic acids.

The aromatic material may be coal, especially bituminous coal, petroleum residium, lignite, peat, pitch, tar, coke, char, oil from oil shale, and any other material containing or capable of evolving or producing aromatic material either liquid or solid.

Any kind of coal, including lignite, anthracite, or coke or char can be used, but bituminous coals give the best yields of benzene carboxylic acids. Yields of benzene carboxylic acids from anthracite coal are low because anthracite is too aromatized. Anthracitic coals produce a product having a high percentage of polynuclear aromatic acids. Yields of aromatic carboxylic acids from lignites are low because lignite produces little aromatic material.

The mixture is treated with oxygen under conditions sufficient to convert the carbonaceous material to carboxylic acid salts or the aromatic material to an aromatic carboxylic acid salt. In general, a temperature of about 200° C. to about 350° C. is required. The pressure in the reaction zone should be sufficient to maintain a liquid state in the reaction zone. Generally this requires a pressure of at least about 250 psig. Preferred reaction zone conditions are about 270° C. and about 900 psig.

Reaction times in the reaction zone depend upon the temperature, degree of agitation, the relative amounts of carbonaceous or aromatic material, water, and a material containing minerals from oil shale or calcined oil shale or mixtures thereof, the solid-to-liquid ratio, and the particle size of the solid materials. Generally, reaction times of from about ten minutes to about three hours are required.

After treating the mixture with oxygen or an oxygen-containing gas such as air to convert the carbonaceous or the aromatic material into carboxylic or aromatic carboxylic acids, and the carboxylic or aromatic carboxylic acids into carboxylic or aromatic carboxylic acid salts, the carboxylic or aromatic carboxylic acid salts are dissolved by treatment of the mixture with an alkaline solution in a dissolving zone.

The alkaline solution can be formed from any salt of a Group Ia element such as sodium hydroxide, potassium hydroxide, sodium carbonate, etc.

The alkaline solution is in sufficient quantity to preferably dissolve all of the carboxylic or aromatic carboxylic acids.

The dissolving zone can be in the same vessel as the reaction zone as may be advantageous in a batch process, or it can be in a separate vessel as is required in a continuous process.

The mixture from the dissolving zone is then introduced to a separation zone where solids comprising the spent material containing minerals from oil shale, or mixture thereof is separated from the dissolved aromatic carboxylic acid salts. Separation of the solids in the separation zone may be by centrifugation, filtration or any other means suitable for removing solids from the mixture.

The dissolved aromatic carboxylic acid salt mixture from the separation zone after solids removal, is then treated in an acidification zone with an acid to convert the aromatic carboxylic acid salts to aromatic carboxylic acids. For example, sodium phthalate treated with mineral acid is converted to phthalic acid and a sodium salt of the mineral acid.

Sufficient acid must be added to the mixture to effect the conversion of the carboxylic acid salts to carboxylic acids or aromatic carboxylic acid salts to aromatic carboxylic acids.

Where the feed material is aromatic, preferably, sufficient acid is added to precipitate any polynuclear carboxylic acids that may be present, such as humic acids, and to leave in solution benzene carboxylic acids. It is especially preferable to add sufficient acid to adjust the pH of the mixture to between about 2 and about 4 to insure the conversion of the acid salts to acids.

Preferably, the conditions in the acidification zone are such that the polynuclear aromatic carboxylic acid will in fact precipitate. These conditions, especially temperature, will vary depending upon the products produced from the oxidation of the particular aromatic carbonaceous material used as a feed material.

The acid used in acidification may be any mineral acid or any organic acid. Sulfuric acid is favored because it is relatively inexpensive.

After forming the carboxylic or aromatic carboxylic acids in the acidification zone, the carboxylic or aromatic carboxylic acids are separated in a separation zone and recovered.

The separation zone may comprise several treating steps and several zones such as extraction, filtration, evaporation, and precipitation.

After the carboxylic or aromatic carboxylic acids are recovered, the remaining mixture is preferably treated to regenerate the alkaline solution employed in the dissolving zone, and the regenerated alkaline solution is recycled to the dissolving zone.

In one embodiment the solids removed from the mixture are calcined to produce at least in part some of the calcined oil shale required for mixing with fresh carbonaceous material and water.

The material containing minerals from oil shale has a catalytic effect on the reaction which produces the carboxylic acid salts.

BRIEF DESCRIPTION OF THE DRAWINGS

The FIGURE is a schematic flow diagram for my process for the production of aromatic carboxylic acid from coal.

DESCRIPTION OF PREFERRED EMBODIMENT

Referring to the FIGURE, a finely divided bituminous coal through stream 10, water through stream 12 and finely divided calcined oil shale through stream 14 are introduced into mixer 20. About five parts water by weight and about 1 to 10 parts by weight of calcined oil shale are added to the mixer per part by weight of coal. Any type of mixer may be used suitable for mixing a slurry containing coal solids. After mixing, the mixture is removed from mixer 20 through stream 22 and introduced into oxidation-reactor or autoclave 30. Air or oxygen is introduced into autoclave 30 through line 24. About two parts by weight of oxygen per part by weight of coal is charged to autoclave 30.

The coal is oxidized in autoclave 30 to produce aromatic carboxylic acids comprising benzene carboxylic acids, polynuclear aromatic acids, carbon dioxide and water. The calcined oil shale produces an alkaline solution by hydrolysis and reacts with the thusly formed acids to produce metal salts thereof.

The autoclave is operated at a temperature of about 200° to about 350° C., preferably about 270° C., and at a pressure of about 250 psig to about 2000 psig, preferably about 900 psig. Temperatures below about 200° C. are not desirable because the formation of polynuclear aromatic carboxylic acids is enhanced and temperatures above about 350° C. are not desirable because the formation of carbon dioxide is enhanced. Pressures outside this range, however, can be used. Lower pressures are not desirable because kinetic rates are lower. Higher pressures are not desirable because of the cost of high pressure equipment and compression costs. Preferably the contents of autoclave 30 are agitated to increase product yield and to lower reaction time. A turbine stirred autoclave is preferred.

Gases comprising carbon dioxide and water vapor are removed from autoclave 30 through line 31 and fed into condenser 35. In condenser 35 the water vapor is condensed. The condensate and gases are removed from condenser 35 through line 36 and fed to separator 37. The condensate is separated from the gas comprising carbon dioxide in separator 37. The gas is removed from separator 37 through line 38 and the condensate through line 39. Both of streams 38 and 39 are useful in subsequent steps in the process as will be described later.

The mixture containing the thusly formed aromatic acid salts are discharged from autoclave 30 through line 32 to cooler 40 where the mixture is cooled to a temperature of about 40° C. Cooler 40 can be any type of cooler such as an agitated tank with cooling plates. The mixture is cooled to facilitate subsequent processing steps which by virtue of the cooling can be performed at ambient or slightly above ambient pressures. It is to be understood that cooling is not necessary to the process and the subsequent steps could be conducted at higher temperatures and pressures if desired.

The cooled mixture is removed from cooler 40 through stream 42 and fed to dissolver 50. An alkaline solution such as sodium hydroxide is fed to dissolver 50 through line 52 in sufficient quantity to dissolve the carboxylic acid salts contained in stream 42. Dissolver 50 can be any type of dissolver such as a stirred tank dissolver. In an embodiment utilizing a batch process, cooler 40 and dissolver 50 may be the same tank. In continuous processes separate apparatuses are required.

The mixture, containing the dissolved aromatic carboxylic acids, is removed from dissolver 50 through line 52 and fed to separator 60 where solid material of the mixture is separated. Separator 60 may be any type of separator such as a centrifuge or a filter. Preferably separator 60 is a precoated revolving drum filter or a vacuum filter. The liquid product containing the dissolved thusly formed aromatic carboxylic acid salts is removed from separator 60 through line 62. The solids which contain unreacted coal and spent calcined oil shale are removed from separator 60 through line 64. The solids can be treated to recover the unreacted coal, which can then be recycled to mixer 20 or autoclave 30. The spent oil shale is then disposed of as for example by landfill utilization.

The filtrate from separator 60 is fed to acidification reactor 70 through line 62. Sufficient acid is added to acidification reactor 70 through line 72 to convert the aromatic carboxylic acid salts to aromatic carboxylic acids. Generally it is preferred to add enough acid to acidification reactor 70 to adjust the pH to between about 2 and about 4, which insures the conversion of the acid salts to acids. Any acid may be used, either organic or mineral. A mineral acid is preferred because of its lower cost. Sulfuric acid is preferred because it is the least costly. Other acid can, of course, be used.

The mixture is removed from acidification reactor 70 through line 74 and fed to separator 80 where the aromatic carboxylic acids are separated from the mixture. Separator 80 can be an extractor separator. An organic extractant, such as methyl-ethyl ketone, is added to separator 80 through line 82. The aromatic carboxylic acids are extracted from the aqueous solution by the extractant. The organic phase containing the aromatic carboxylic acids and organic extractant is removed from separator 80 through line 84 and the aqueous phase containing the salt of the alkaline solution in line 52 and the acid in line 72 is removed through line 86. In this embodiment the salt is sodium sulfate. Separator 80 may be any type of separator such as a decanter, plate tower, packed tower, or rotary-disk contactor-separator.

The organic phase containing the aromatic carboxylic acids are fed to separator 90 where any higher molecular weight carboxylic acids, such as humic acids, which have precipitated in the organic phase are separated from the organic phase. Separator 90 may be any type of solid-liquid separator such as a centrifuge or a filter.

The separated higher molecular weight carboxylic acids and any other solids which may be present are removed from separator 90 through line 92 and recycled to oxidation reactor 30 to produce lower molecular weight aromatic carboxylic acids.

The organic phase containing the dissolved aromatic carboxylic acids are removed from separator 90 through line 94 and fed to separator 100.

In separator 100, the organic extractant is separated from the aromatic carboxylic acids. Separator 100 may be an evaporator or any distillation or fractionation apparatus suitable for separating the aromatic carboxylic acids either in one stream or several component streams from the organic extractant. The organic extractant is removed from separator 100 through line 102 and recycled to separator 80.

The separated aromatic carboxylic acids are removed through line 104 and collected in storage vessel 110. Although the aromatic carboxylic acids are shown as one stream it is understood that several types or mixtures of aromatic carboxylic acid may be collected as separate streams, rather than just one stream, if separator 100 were a fractionator.

The aqueous stream 86 removed from separator 80 is fed to precipitator 120 together with lime introduced to the precipitator through line 122. In precipitator 120 the aqueous solution of sodium sulfate reacts with the lime to produce sodium hydroxide solution and calcium sulfate precipitate. The mixture is removed from precipitator 120 through line 124 and fed to separator 130.

In separator 130 the calcium sulfate is separated from the sodium hydroxide solution. Separator 130 may be any type of solid-liquid separator such as a centrifuge or filter. The calcium sulfate precipitate is removed through line 132 and collected in storage vessel 140. The calcium sulfate may be used in the making of portland cement, gypsum or pool acid or disposed of by landfill. The aqueous solution of sodium hydroxide is removed from separator 130 through line 134 and recycled to dissolver 50.

The aromatic carboxylic acid collected in storage vessel 110 can be isomerized to produce value products such as terephthalic acid by conventional methods. In such cases gaseous stream 38 from separator 37 which contains carbon dioxide can be utilized to pressurize the isomerization reactor.

Condensate stream 39 can be recycled to mixer 20 to supply at least in part the water requirements for the mixing operation.

EXAMPLE 28 gr of bituminous coal was mixed with 150 gr of powdered, spent oil shale (that had been calcined in a retort to remove oil) and 400 cm$^3$ of water. This was introduced into a 2 liter autoclave and pressurized to 300 psig and heated to 240° C. Further oxygen was added to attain a total pressure of 1200 psig. The autoclave was kept at 240° C. for approximately 30 minutes. The mixture was agitated during this time with a stirrer at 1100 r.p.m. Carbon dioxide was periodically vented from the autoclave. After cooling and removal of the autoclave contents, 10.6 gr of aromatic carboxylic acids were separated from the reacted mixture. This represents a 46% moisture-ash-free yield. Of this 10.6 gr, 1.2 gr were found to be benezenecarboxylic acids, and 9.4 gr were found to be polynuclear aromatic acids.

An analysis of the calcined oil shale as used in this example is as follows:

| COMPONENT | WEIGHT % |
| --- | --- |
| $SiO_2$ | 43.2 |
| $Al_2O_3$ | 7.80 |
| $Fe_2O_3$ | 3.37 |
| $TiO_2$ | 0.40 |
| $P_2O_5$ | 0.23 |
| CaO | 13.75 |
| MgO | 2.62 |
| $Na_2O$ | 1.87 |
| $K_2O$ | 2.51 |
| $SO_3$ | 1.27 |
| Organic Carbon | 0.62 |
| Carbonate Carbon | 3.30 |
| Alkalinity | 29.0 |
| Total % | 80.94 |

By alkalinity as referred to in the above table is meant the total alkali content determined by acid titration and expressed as $Na_2O$.

The process of the invention has been described generally and by example with reference of clarity and illustration only. It will be apparent to those skilled in the art from the foregoing that various modifications of the process and the materials disclosed herein can be made without departure from the spirit of the invention.

Accordingly, the invention is not to be construed or limited to the specific embodiments illustrated, but only as defined in the following claims.

I claim:

1. A process for producing benzene carboxylic acid salt from carbonaceous material comprising treating a mixture of
i. a carbonaceous material selected from the group consisting of coal, petroleum residium, lignite, peat, pitch, tar, coke, char, oil from oil shale and mixtures thereof,
ii. water, and
iii. a calcined oil shale with oxygen, at a temperature of from about 200° to about 350° C., a pressure of from about 250 to about 2000 psig, and a reaction time of from about 10 minutes to about 3 hours, to convert said carbonaceous material to a benzene carboxylic acid salt; and recovering said benzene carboxylic acid salt.

2. A process for producing benzene carboxylic acid from carbonaceous material comprising treating a mixture of
i. a carbonaceous material selected from the group consisting of coal, petroleum residium, lignite, peat, pitch, tar, coke, char, oil from oil shale and mixtures thereof,
ii. water, and
iii. a calcined oil shale with oxygen, at a temperature of from about 200° to about 350° C., a pressure of from about 250 to about 2000 psig, and a reaction time of from about 10 minutes to about 3 hours, to convert said carbonaceous material to a benzene carboxylic acid salt; treating said benzene carboxylic acid salt with an acid to convert said benzene carboxylic acid salt to a benzene carboxylic acid; and recovering said benzene carboxylic acid.

3. A process for producing benzene carboxylic acid from carbonaceous material comprising:
a. treating a mixture of
i. a carbonaceous material selected from the group consisting of coal, petroleum residium, lignite, peat, pitch, tar, coke, char, oil from oil shale and mixtures thereof,
ii. water, and
iii. a calcined oil shale with oxygen, at a temperature of from about 200° to about 350° C., a pressure of from about 250 to about 2000 psig, and a reaction time of from about 10 minutes to about 3 hours, to convert said carbonaceous material to a benzene carboxylic acid salt thereby producing a second mixture containing dissolved therein said benzene carboxylic acid salt;
b. removing solids comprising said calcined oil shale from said second mixture thereby producing a solution;
c. treating said solution with an acid to convert said benzene carboxylic acid salt dissolved therein to a benzene carboxylic acid thereby producing a third mixture; and
d. recovering said benzene carboxylic acid thusly produced from said third mixture.

4. A process for producing benzene carboxylic acid from carbonaceous material comprising:
a. treating in an oxidation zone a mixture of
i. a carbonaceous material selected from the group consisting of coal, petroleum residium, lignite, peat, pitch, tar, coke, char, oil from oil shale and mixtures thereof,
ii. water, and
iii. a calcined oil shale with oxygen, at a temperature of from about 200° to about 350° C., a pressure of from about 250 to about 2000 psig, and a reaction time of from about 10 minutes to about 3 hours, to convert said carbonaceous material to benzene carboxylic acid salt thereby producing a second mixture containing dissolved therein a first portion of said benzene carboxylic acid salt, said second mixture containing as an undissolved solid a second portion of said benzene carboxylic acid salt;
b. dissolving said undissolved benzene carboxylic acid salt produced in said oxidation zone with an alkaline solution in a dissolving zone thereby producing a third mixture;

c. removing solids comprising said calcined oil shale from said third mixture from said dissolving zone thereby producing a first solution;

d. treating said first solution with an acid to convert said benzene carboxylic acid salt dissolved therein to a benzene carboxylic acid; and e. recovering said benzene carboxylic acid thusly formed.

5. The process of claim 4 wherein said alkaline solution comprises sodium hydroxide.

6. The process of claim 4 wherein said acid is sulfuric acid.

7. The process of claim 4 further comprising separating solid carbonaceous material in said solids removed from said third mixture and recycling said separated solid carbonaceous material to said oxidation zone for further treating.

8. A process for producing benzene carboxylic acid from coal comprising:

a. treating in an oxidation zone a mixture of coal, water, and calcined oil shale with oxygen, at a temperature of from about 200° to about 350° C., a pressure of from about 250 to about 2000 psig, and a reaction time of from about 10 minutes to about 3 hours, wherein the amount of said calcined oil shale is about 1 to about 10 parts by weight of said calcined oil shale per part by weight of said coal, to convert said coal to a benzene carboxylic acid salt thereby producing a second mixture containing dissolved therein said benzene carboxylic acid salt;

b. removing solids comprising said calcined oil shale from said second mixture thereby producing a solution;

c. treating said solution with an acid to convert said benzene carboxylic acid salt dissolved therein to a benzene carboxylic acid; and d. recovering said benzene carboxylic acid thusly formed.

9. The process of claim 4 wherein said carbonaceous material is coal.

10. The process of claim 9 wherein said alkaline solution comprises sodium hydroxide.

11. The process of claim 8 wherein said coal is bituminous coat.

12. The process of claim 8 further comprising separating a solid aromatic material, which comprises unreacted coal from said solids removed from said second mixture and recycling said separated solid aromatic material to said oxidation zone for further treating.

13. The process of claim 4 further comprising, after recovering said benzene carboxylic acid from said first solution, regenerating said alkaline solution by treating said first solution with lime, and recycling said alkaline solution thusly regenerated to said dissolving zone.

14. The process of claim 8 wherein said acid is sulfuric acid.

15. A process for producing benzene carboxylic acid from aromatic material comprising:

a. treating in an oxidation zone a mixture of
 i. an aromatic material selected from the group consisting of coal, petroleum residium, lignite, peat, pitch, tar, coke, char, oil from oil shale and mixtures thereof,
 ii. water, and
 iii. finely divided calcined oil shale with oxygen, at a temperature of from about 200° to about 350° C., a pressure of from about 250 to about 2000 psig, and a reaction time of from about 10 minutes to about 3 hours, to convert said aromatic material to benzene carboxylic acid salt thereby producing a second mixture containing dissolved therein a first portion of said benzene carboxylic acid salt, said second mixture containing as an undissolved solid a second portion of said benzene carboxylic acid salt;

b. dissolving said undissolved benzene carboxylic acid salt produced in said oxidation zone with aqueous sodium hydroxide thereby producing a third mixture;

c. removing solids comprising said finely divided calcined oil shale from said third mixture thereby producing a first solution;

d. treating said first solution with sulfuric acid to convert said benzene carboxylic acid salt dissolved therein to a benzene carboxylic acid; and e. recovering said benzene carboxylic acid thusly formed.

16. The process of claim 15 wherein said aromatic material is coal.

17. The process of claim 15 wherein said aromatic material is bituminous coal.

18. A process for producing benzene carboxylic acid from aromatic material comprising:

a. treating in an oxidation zone a mixture of
 i. an aromatic material selected from the group consisting of coal, petroleum residium, lignite, peat, pitch, tar, coke, char, oil from oil shale and mixtures thereof,
 ii. a polynuclear aromatic carboxylic acid,
 iii. water, and
 iv. a finely divided calcined oil shale with oxygen at a temperature of from about 200° to about 350° C., a pressure of from about 250 to about 2000 psig, and a reaction time of from about 10 minutes to about 3 hours, to convert said aromatic material to benzene carboxylic acid salt thereby producing a second mixture containing dissolved therein a first portion of said benzene carboxylic acid salt, said second mixture containing as an undissolved solid a second portion of said benzene carboxylic acid salt;

b. dissolving said undissolved benzene carboxylic acid salt produced in said oxidation zone with an alkaline solution in a dissolving zone thereby producing a third mixture;

c. removing solids comprising said finely divided calcined oil shale from said third mixture thereby producing a first solution;

d. treating said first solution in an acidification zone with an acid to adjust the pH of said first solution to between about 2 and about 4 to convert said benzene carboxylic acid salt dissolved therein to benzene carboxylic acid, and to precipitate polynuclear aromatic carboxylic acid thereby producing a fourth mixture;

e. separating said polynuclear aromatic carboxylic acid from said fourth mixture;

f. recycling said polynuclear aromatic carboxylic acid thusly separated to said oxidation zone as said polynuclear aromatic carboxylic acid of said mixture; and g. recovering said benzene carboxylic acid from said fourth mixture.

19. The process of claim 18 wherein said aromatic material is coal.

20. The process of claim 18 wherein said aromatic material is bituminous coal.

21. The process of claim 18 wherein said acid utilized in said acidification zone comprises sulfuric acid.

22. The process of claim 18 wherein carbon dioxide is formed in said oxidation zone and further comprising removing a gas stream comprising carbon dioxide from said oxidation zone.

23. The process of claim 18 wherein said alkaline solution comprises sodium hydroxide.

24. The process of claim 18 further comprising, after separating said polynuclear aromatic carboxylic acid from said fourth mixture, regenerating said alkaline solution by treating said fourth mixture with lime, and recycling said alkaline solution thusly regenerated to said dissolving zone.

25. The process of claim 18 wherein said aromatic material is bituminous coal, said alkaline solution comprises sodium hydroxide, and said acid is sulfuric acid.

26. A process for producing benzene carboxylic acid from coal comprising:
 a. treating in an oxidation zone a mixture comprising coal, a polynuclear aromatic carboxylic acid, water, and finely divided calcined oil shale with oxygen at a temperature of from about 200° to about 350° C., a pressure of from about 250 to about 2000 psig, and a reaction time of from about 10 minutes to about 3 hours, wherein the amount of said finely divided calcined oil shale is about 1 to about 10 parts by weight of said finely divided calcined oil shale per part by weight of said coal, to convert said coal to benzene carboxylic acid salt thereby producing a second mixture containing dissolved therein a first portion of said benzene carboxylic acid salt, said second mixture containing as an undissolved solid a second portion of said benzene carboxylic acid salt;
 b. dissolving said undissolved benzene carboxylic acid salt produced in said oxidation zone with an alkaline solution in a dissolving zone thereby producing a third mixture;
 c. removing solids comprising said finely divided calcined oil shale from said third mixture thereby producing a first solution;
 d. treating said first solution in an acidification zone with an acid to adjust the pH of said first solution to between about 2 and about 4 to convert said benzene carboxylic acid salt dissolved therein to benzene carboxylic acid, and to precipitate polynuclear aromatic carboxylic acid thereby producing a fourth mixture;
 e. treating in an extraction zone said fourth mixture from said acidification zone with an organic liquid extractant to extract said benzene carboxylic acid and to form an organic phase comprising said organic liquid extractant, said benzene carboxylic acid, and said precipitated polynuclear aromatic carboxylic acid and an aqueous phase comprising a cation of said alkaline solution utilized in said dissolving zone;
 f. separating in a first separation zone said organic phase from said aqueous phase;
 g. separating said precipitated polynuclear aromatic carboxylic acid from said organic phase;
 h. recycling said polynuclear aromatic carboxylic acid thusly separated to said oxidation zone as said polynuclear aromatic carboxylic acid of said mixture;
 i. separating in a second separation zone said benzene carboxylic acid from said organic phase;
 j. treating said aqueous phase from said first separation zone with lime to regenerate said alkaline solution;
 k. recycling said alkaline solution thusly regenerated to said dissolving zone as said alkaline solution; and
 l. recycling said organic phase separated from said aromatic carboxylic acid in said second separation zone to said extraction zone as said organic liquid extractant.

27. The process of claim 26 wherein said alkaline solution utilized in said dissolving zone is sodium hydroxide; wherein said acid utilized in said acidification zone is sulfuric acid; and wherein aid coal is bituminous coal.

* * * * *